United States Patent
Levine et al.

(10) Patent No.: US 7,308,310 B1
(45) Date of Patent: Dec. 11, 2007

(54) IMPLANTABLE CARDIAC STIMULATION DEVICE PROVIDING BIPOLAR AUTOCAPTURE AND LEAD IMPEDANCE ASSESSMENT AND METHOD

(75) Inventors: Paul A. Levine, Santa Clarita, CA (US); Arndt Godau, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 117 days.

(21) Appl. No.: 11/045,627

(22) Filed: Jan. 26, 2005

(51) Int. Cl.
*A61N 1/08* (2006.01)
(52) U.S. Cl. .................................. 607/28
(58) Field of Classification Search ............. 607/27, 607/28
See application file for complete search history.

(56) References Cited

U.S. PATENT DOCUMENTS

| | | | |
|---|---|---|---|
| 4,140,131 A | 2/1979 | Dutcher et al. | 128/419 PT |
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | |
| 4,729,376 A | 3/1988 | DeCote, Jr. | 128/419 PT |
| 4,788,980 A | 12/1988 | Mann et al. | |
| 4,940,052 A | 7/1990 | Mann et al. | |
| 4,944,298 A | 7/1990 | Sholder | |
| 4,969,467 A | 11/1990 | Callaghan et al. | 128/419 PG |
| 5,003,975 A | 4/1991 | Hafelfinger et al. | 128/419 PG |
| 5,350,410 A | 9/1994 | Kleks et al. | 607/28 |
| 5,466,254 A | 11/1995 | Helland | |
| 5,476,483 A | 12/1995 | Bornzin et al. | |
| 5,476,485 A | 12/1995 | Weinberg et al. | 607/28 |
| 5,814,088 A | 9/1998 | Paul et al. | 607/28 |
| 5,855,594 A | 1/1999 | Olive et al. | 607/28 |

(Continued)

FOREIGN PATENT DOCUMENTS

EP 0 338 363 A2 10/1989

(Continued)

OTHER PUBLICATIONS

Binner, Ludwig et al., "*Autocapture Enhancements: Unipolar and Bipolar Lead Compatibility and Bipolar Pacing Capability on Bipolar Leads*," PACE 2003; 26[Pt. II]):221-224.

(Continued)

*Primary Examiner*—Mark Bockelman
*Assistant Examiner*—Eric D. Bertram

(57) ABSTRACT

An implantable cardiac stimulation device provides bipolar pacing and bipolar autocapture. If a measured bipolar electrode configuration capture threshold is too high, an impedance measuring circuit measures the impedance of the bipolar electrode configuration to determine a possible lead failure. If the bipolar electrode configuration impedance is within a normal range, bipolar pacing is continued in a manner which assures continued capture of the heart. If the bipolar electrode configuration impedance is outside of the given range of impedances, the device is switched to unipolar pacing in a manner which insures capture of the heart and notification of the need for a physician consultation.

13 Claims, 5 Drawing Sheets

U.S. PATENT DOCUMENTS

| | | |
|---|---|---|
| 6,327,498 B1 | 12/2001 | Kroll |
| 6,430,441 B1 | 8/2002 | Levine ............ 607/28 |
| 6,546,288 B1 * | 4/2003 | Levine ............ 607/28 |
| 7,031,773 B1 | 4/2006 | Levine et al. |
| 2002/0147477 A1 | 10/2002 | Pons et al. |

FOREIGN PATENT DOCUMENTS

| | | |
|---|---|---|
| EP | 0 338 363 A3 | 10/1989 |
| EP | 0 338 363 B1 | 10/1989 |
| EP | 0 338 364 B1 | 10/1989 |
| EP | 0770408 B1 | 3/2004 |
| WO | 0020071 | 8/2007 |

OTHER PUBLICATIONS

Clarke, Malcolm et al., "*Automatic Adjustment of Pacemaker Stimulation Output Correlated with Continuously Monitored Capture Thresholds: A Multicenter Study*," PACE 1998; 21: 1567-1575.

Dorwarth, Uwe MD et al., "Transvenous Defibrillation Leads: High Incidence of Failure During Long-Term Follow-Up," J. Cardiovasc Electrophysiol. 2003;14:38-43.

First Office Action, mailed Jul. 27, 2005: Related Application.

Notice of Allowance, mailed Nov. 30, 2005: Related Application.

\* cited by examiner

IMPLANTABLE CARDIAC STIMULATION DEVICE PROVIDING BIPOLAR AUTOCAPTURE AND LEAD IMPEDANCE ASSESSMENT AND METHOD

FIELD OF THE INVENTION

The present invention generally relates to an implantable cardiac stimulation device that provides electrical therapy to a patient's heart. The present invention more particularly relates to such a device that automatically performs autocapture in a bipolar electrode configuration and lead impedance evaluations.

BACKGROUND

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator. A pacemaker is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. Usually the electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events represented as P waves on the surface electrocardiogram (ECG) and intrinsic ventricular events represented as R waves on the surface ECG. The pacemaker, however, does not use the surface ECG electrical events but uses the signal as identified inside the heart. This is termed an electrogram. It would be an atrial EGM (AEGM) for the native atrial depolarization and a ventricular EGM (VEGM) for a native ventricular depolarization. By monitoring such AEGM and VEGM, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

The energies of the applied pacing pulses are selected to be above the pacing energy stimulation threshold of the respective heart chamber to cause the heart muscle of that chamber to depolarize or contract. If an applied pacing pulse has an energy below the pacing energy stimulation threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the pacing energy stimulation threshold.

However, it is also desirable to employ pacing energies which are not exorbitantly above the stimulation threshold. The reason for this is that pacemakers are implanted devices and rely solely on battery power. Using pacing energies that are too much above the stimulation threshold would result in early depletion of the battery and hence premature device replacement. Prior to autocapture, the capture threshold would be assessed at the periodic follow-up visits with the physician and the output of the pacemaker adjusted (programmed) to a safety margin that was appropriate based on the results of that evaluation. However, capture thresholds may change between scheduled follow-up visits with the physician. A refinement of the technique of periodic capture threshold measurements by the physician was the automatic performance of capture threshold assessment and the automatic adjustment of the output of the pulse generator. Capture threshold may be defined in terms of pulse amplitude, either voltage or current, pulse duration or width, pulse energy, pulse charge or current density. The parameters that can be easily adjusted by the clinician are pulse amplitude and pulse width. With the introduction of autocapture, the implanted pacing system may periodically and automatically assesses the capture threshold and then adjusts the delivered output. It also monitors capture on a beat-by-beat basis such that a rise in capture threshold will be recognized allowing the system to compensate by delivery initially of higher-output back-up or safety pulses and then incrementing the output of the primary pulse until stable capture is again demonstrated. The output amplitude of the pacing stimulus is set slightly above the measured capture threshold minimizing battery drain while the patient is protected by the significantly higher output back-up safety pulse. These evaluations are often referred to as autocapture tests or simply autocapture.

As is well known in the art, the stimulation threshold of a heart chamber can, for various reasons, change over time. Hence, pacemakers that incorporate autocapture are generally able to periodically and automatically perform autocapture tests. In this way, the variations or changes in stimulation threshold can be accommodated.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" or "loss of capture" of the heart.

When a pacemaker performs an autocapture test, its pulse generator applies a succession of primary pacing pulses to the heart at a basic rate. The output of the primary pulse is progressively reduced. In one known system, there will be a minimum of two consecutive pulses at a given energy before the output associated with the primary pulse is reduced or increased. The output of successive primary pacing pulses is reduced by a known amount and capture is verified following each pulse. If a primary pulse results in loss of capture, a backup or safety pulse is applied to sustain heart activity. If there is loss of capture associated with the primary pulse on two successive cycles, this is interpreted as being subthreshold. At that time, the output associated with the primary pulse is progressively increased in small increments until capture is confirmed on two consecutive primary pulses. This, of course, is but one example. As is known in the art, a single pulse or any number of pulses may be used to establish the capture threshold. The lowest output setting that results in capture on consecutive pulses starting from a low value where there is loss of capture is defined as the capture threshold. A most recent system then automatically adjusts the output with a working margin of an additional 0.25 Volts. In these methods, capture may be verified by detecting the evoked response associated with the output pulse, the T-waves or repolarization waves associated with the electrical depolarization, mechanical heart contraction, changes in cardiac blood volume impedance, or another signature of a contracting chamber.

Loss of capture can have many different causes. A common cause involves lead failure. Lead failure may result, for example, when the two conductors of a bipolar pacing lead become shorted together. Another lead failure may involve an open circuit where the continuity of one or both conductors in a bipolar lead is disrupted. In the event of either occurrence, switching from a bipolar pacing polarity electrode configuration to a unipolar pacing polarity electrode configuration may restore stimulation effectiveness.

Pacemakers are also capable of sensing. When programmed to the bipolar sensing configuration, the signal that is detected is the voltage difference between the two active electrodes inside the heart. In a unipolar sensing configuration, the signal that is detected is the voltage difference between one electrode in the heart and an electrode located elsewhere. Most commonly, the other electrode is the metallic housing of the pulse generator. Unipolar sensing can also be further specified as being between the electrode tip inside the heart and the housing of the pulse generator or between the proximal ring electrode that is set back from the tip and the housing of the pulse generator.

In the past, autocapture has been performed with unipolar primary pacing pulses, bipolar backup pulses, and bipolar evoked response sensing. Since bipolar pacing is generally preferred over unipolar pacing, it would be most desirable to be able to use bipolar primary pacing pulses during autocapture. The use of bipolar primary pacing pulses requires a new approach to handling autocapture and the continued safe pacing of the patient. It would also be desirable to be able to maintain autocapture in a unipolar electrode configuration should a bipolar lead experience a failure on one of the conductors.

While autocapture is generally used with ventricular leads, it may be used with atrial leads as well. Hence, it is to be understood that the invention is applicable for either atrial and/or ventricular leads.

Pacemakers are known having lead supervision wherein lead impedance is measured on either a beat-to-beat or more commonly, a periodic basis. If the bipolar lead impedance is above or below a certain threshold, the pacing configuration may be automatically switched to a unipolar pacing configuration.

Impedance measurement on a beat-to-beat basis increases the power consumption of the implanted device and consequently reduces the longevity of the device. Assessing lead impedance, also called stimulation impedance, has the same limitations as assessing the capture threshold on a periodic but infrequent basis. Problems may be manifest between scheduled evaluations leaving the patient unprotected if a problem were to develop. Still further, since a mechanical problem developing in a lead is likely to be manifest in the bipolar configuration first, an early manifestation of a lead malfunction may not be appreciated if autocapture were to be enabled with primary pacing pulses in a unipolar electrode configuration. Still further, if a problem were detected, reverting to the unipolar sensing configuration based upon lead impedance may require that autocapture be disabled. The present invention addresses these issues by providing an implantable cardiac device capable of providing autocapture with bipolar primary pacing pulses while maintaining lead supervision when required. The invention also permits maintenance of autocapture, but in a unipolar electrode configuration, if a configuration switch is required, and most importantly, continued stimulation of the heart in the event of a lead failure.

SUMMARY

What is described herein is an implantable cardiac device comprising a pulse generator that provides pacing stimulation pulses; a sensing circuit that senses cardiac activity; and a lead system that provides a bipolar electrode configuration and a unipolar electrode configuration associated with a chamber of a heart. The pulse generator and sensing circuit provide pacing therapy with the bipolar electrode configuration. The device further comprises a capture threshold assessment circuit that measures capture threshold and that couples the pulse generator and sensing circuit to the bipolar electrode configuration to provide bipolar primary pulses, bipolar backup pulses and bipolar evoked response sensing, and an impedance measuring circuit that measures impedance of the bipolar electrode configuration responsive to the assessment circuit measuring a capture threshold above a preset threshold value.

The device may further comprise a comparison circuit that determines if the impedance of the bipolar electrode configuration is within a given range. The device may further comprise an output control that increases pulse generator output responsive to the impedance being within the given range. The output control preferably increases pulse generator output to a maximum level. It may do so if, for example, the threshold was measured to be above a set threshold value and the lead impedance was assessed to be within the given range. The capture threshold assessment circuit may then periodically measure the capture threshold responsive to the output control increasing the pulse generator output. The output control may then adjust the pulse generator output when the measured capture threshold is below a set threshold value.

The capture threshold assessment circuit may determine if the unipolar capture threshold is below a given threshold. The capture threshold assessment circuit may adjust the pulse generator output, if the capture threshold is below the given threshold. If the unipolar capture threshold is above the given threshold, the capture threshold assessment circuit may be disabled. The output control may then increase pulse generator output responsive to the capture threshold assessment circuit being disabled.

In another embodiment, a method is described comprising providing pacing stimulation therapy to a chamber of a heart with a bipolar electrode configuration, determining if capture threshold by the bipolar electrode configuration is above a preset threshold value, and measuring bipolar electrode configuration impedance if the capture threshold is above the preset value.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
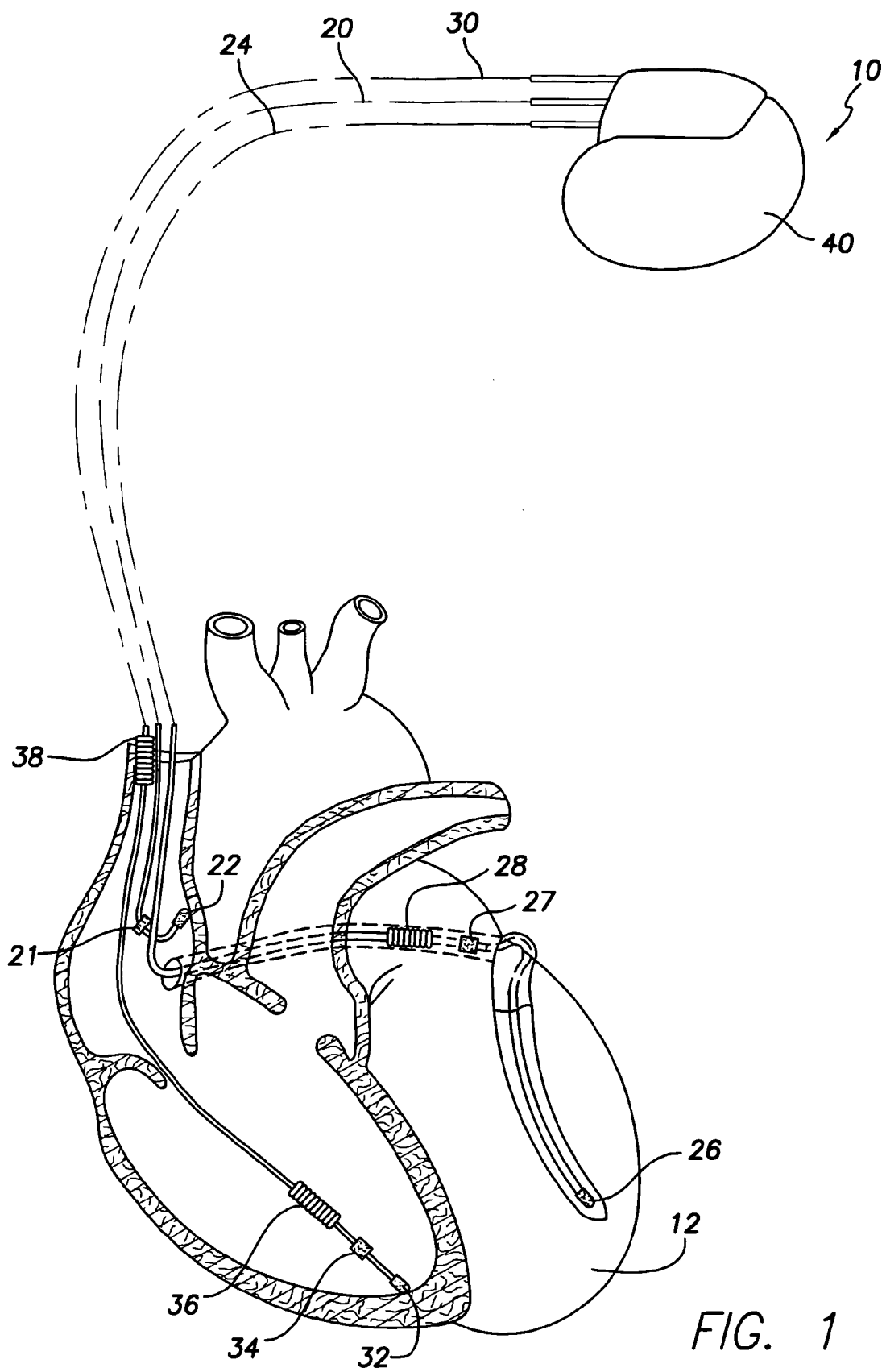
FIG. 1 is a simplified diagram illustrating an implantable cardiac stimulation device in electrical communication with a patient's heart for delivering multi-chamber stimulation and shock therapy.

As shown in FIG. 1, there is a stimulation system including a device 10 and three leads, 20, 24 and 30, coupling the device to a patient's heart 12 for delivering multi-chamber stimulation and shock therapy. To sense atrial cardiac signals and to provide right atrial chamber stimulation therapy, the stimulation device 10 is coupled to an implantable right atrial lead 20 having an atrial ring electrode 21 and an atrial tip electrode 22, which typically are implanted in the patient's right atrial appendage, although they may be positioned in any location in the atrium. The electrodes 21 and 22 may be used as a bipolar electrode pair for bipolar pacing of the right atrium. Alternatively, either electrode 21 or electrode 22 (preferably electrode 22) may be used with the case of the device 10 for unipolar pacing of the right atrium.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. For pacing the right ventricle, the electrodes 32 and 34 may be used together for bipolar pacing or alternatively, either electrode 32 or electrode 34 (preferably electrode 32) may be used with the case 40 of the device 10 for unipolar pacing.

Figure 2:
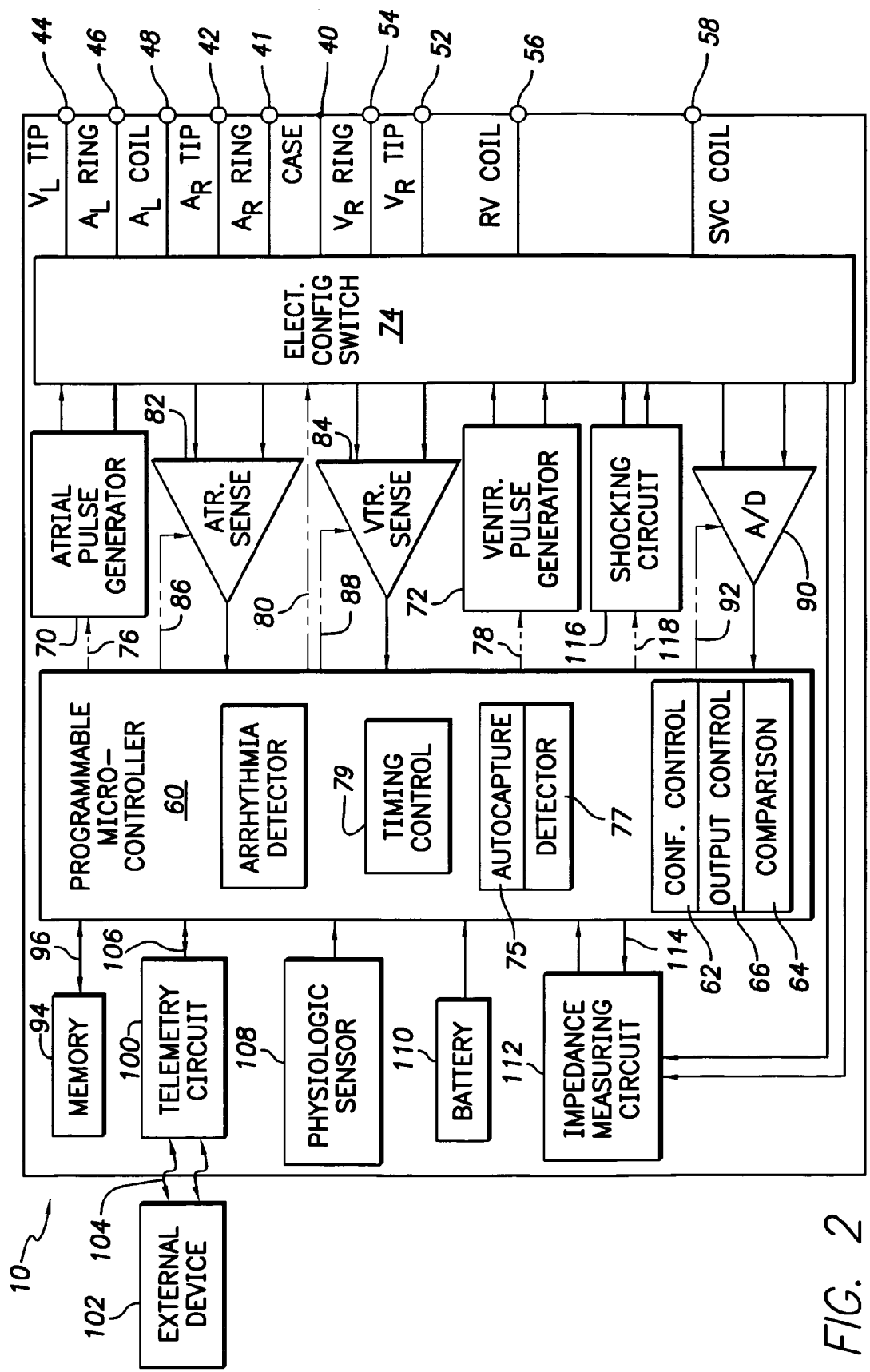
FIG. 2 is a functional block diagram of a multi-chamber implantable stimulation device illustrating the basic elements thereof for providing cardioversion, defibrillation and pacing stimulation in four chambers of the heart as well as autocapture and lead impedance surveillance in accordance with an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes and pacing polarity electrode configurations. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal ($A_R$ RING) 41 adapted for connection to the right atrial ring electrode 21.

Alternatively to the mentioned intravenous leads epicardial leads could be used instead of one or more of the intravenous leads.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, additional elements and functions within the device as they more particularly pertain to this embodiment of the present invention will now be described. The microcontroller includes an autocapture circuit or stage 75. With respect to autocapture, the data acquisition system 90 may be coupled to the microcontroller and include dedicated detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The autocapture 75 includes an evoked response detector 77 that detects a depolarization signal during a window following a stimulation pulse, the presence of which indicates that capture has occurred. The autocapture 75 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window. The evoked response detector 77 processes the data provided by the data acquisition system 90 and, based on the amplitude, determines if an evoked response and hence capture has occurred. Capture detection may occur on a beat-by-beat basis or on a sampled basis. Also, capture detection may be performed for either ventricular or atrial pacing.

In accordance with this embodiment, a capture threshold search is performed on a periodic basis, preferably performed once a day, if the system is stable. A capture threshold search would begin with a small increase in pacing rate (usage with a dual or multi chamber device in the atrium or with a single chamber device) or a shortening of the AV/PV delay (usage with a dual or multi chamber device in the ventricle) if the system were otherwise inhibited or at the functional rate if output stimuli are being delivered and at a desired starting point (either a high energy level or the level at which capture is currently occurring) and decrease the output level until capture is lost. At each output level, the pulse generator provides a primary pacing pulse using a bipolar electrode configuration. To this end, the autocapture 75 advantageously controls the coupling of the pulse generator 72 and data acquisition system 90 to the bipolar electrode configuration to provide bipolar primary pulses, bipolar backup pulses, and bipolar evoked response sensing. If an evoked response (capture) is detected, the energy of the next series of primary pacing pulses is decremented. If an evoked response is not detected (capture lost), the primary pacing pulse is followed, fifty to one-hundred milliseconds thereafter, by a backup pacing pulse also using a bipolar electrode configuration and at a higher energy to assure capture and contraction of the heart chamber. The system then begins to increase the output associated with the primary pulse. The value at which capture is regained is known as the capture threshold. Thereafter, to complete an autocapture assessment, a working margin is added to the capture threshold to set the pacing output. As previously noted, the foregoing autocapture procedure applies equally as well to atrial capture threshold assessment.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); U.S. Pat. No. 5,350,410 (Kleks et al.); and U.S. Pat. No. 6,430,441 (Levine), which patents are hereby incorporated herein by reference. The type of capture detection system used is not critical to the present invention.

As further shown in FIG. 2, and in accordance with the present invention, the device 10 includes an impedance measuring circuit 112 which is enabled by the microcontroller 60 via a control signal 114. In accordance with this embodiment of the present invention the impedance measuring circuit is enabled whenever a capture threshold above a present threshold level is measured during an autocapture capture threshold assessment using a bipolar electrode configuration for the primary pulses, the backup pulses, and evoked response detection. More particularly, the impedance measuring circuit 112 measures the lead impedance of the bipolar pacing electrode configuration during the backup pulse to determine if lead failure is a possible reason for the high capture threshold. The impedance measuring circuit 112 is advantageously coupled by switch 74 under control of configuration control 62 to the bipolar pacing electrode configuration. A comparison circuit 64 determines if the measured impedance falls outside of a predetermined or programmable impedance range, as for example less than 200 ohms or greater than 2000 ohms. If it does, a possible lead failure is noted and the autocapture 75 takes further action to respond to the abnormal impedance measurement to assure continued pacing and safety of the patient. One such response is for configuration control 62 to cause the switch 74 to switch the pacing electrode configuration to a unipolar pacing electrode configuration. As will be seen subsequently, the autocapture 75 may then conduct an autocapture test with the unipolar pacing electrode configuration. In completing the unipolar capture test, the autocapture 75 preferably provides the working margin and then enables continued pacing in the unipolar pacing electrode configuration. In another embodiment, an output control 66 increases the output to a much higher value to assure capture with the unipolar pacing electrode configuration. In this setting, the autocapture 75 would then be disabled. Other variations and embodiments for responding to an abnormal bipolar electrode configuration impedance measurement will be described subsequently with reference to the subroutines of FIGS. 4-6.

As will also be seen subsequently, if the bipolar electrode configuration falls within the given impedance range, the autocapture 75 takes different action to assure pacing and safety of the patient. Here, the output is increased by output control 66 to a high level, such as a maximum level, to assure capture. Thereafter, the autocapture assesses the capture threshold. When it falls below a preset value, the output may be decreased and set to a more normal level as dictated by the threshold and safety margin.

Figure 3:
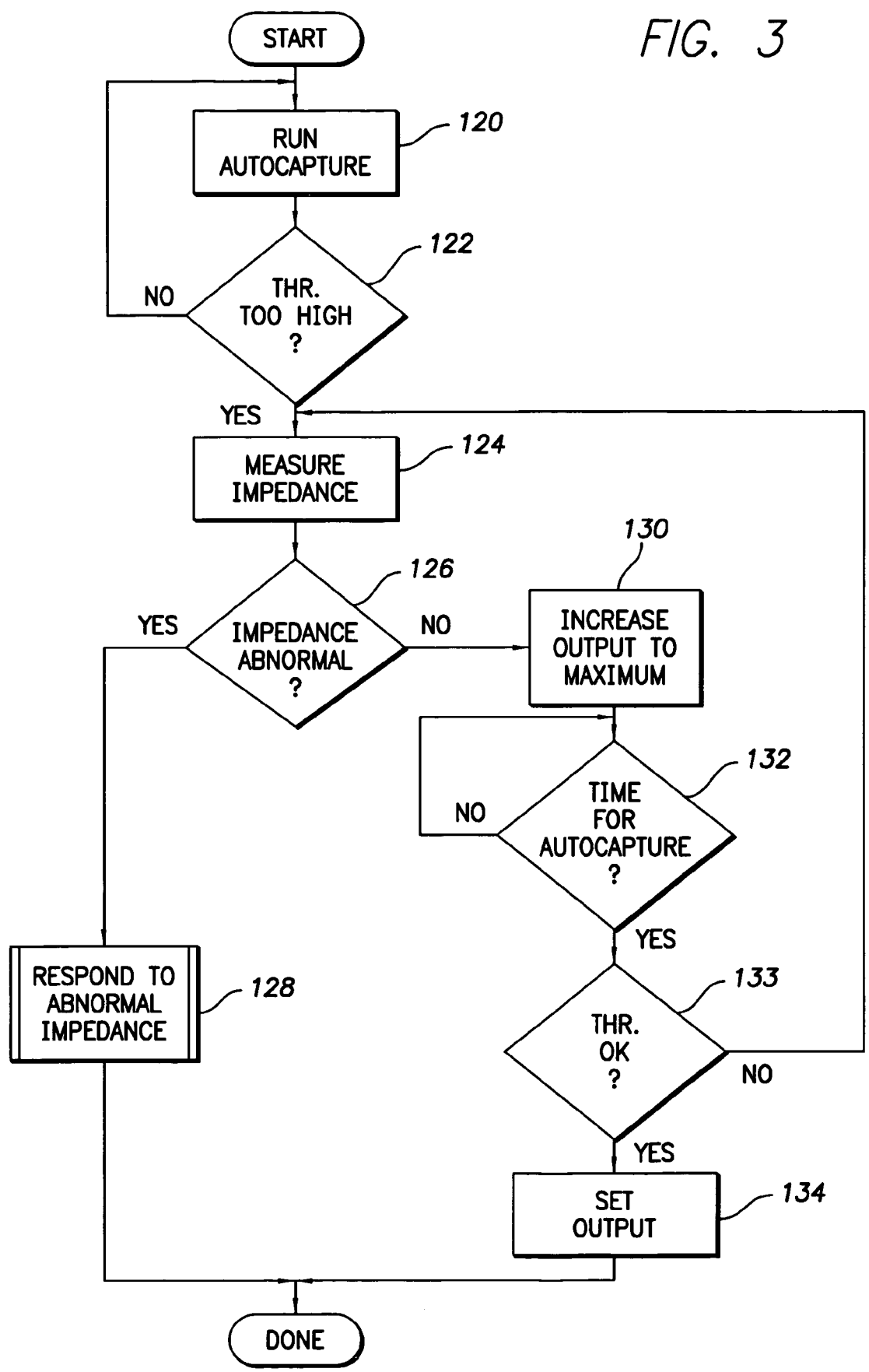
FIG. 3 is a flow chart describing an overview of the operation of one embodiment.

In FIG. 3, a flow chart is shown describing an overview of the operation and novel features implemented in one embodiment of the device 10. In this flow chart, and the subroutine flow charts of FIGS. 4-6, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with activity block 120 with the initiation of autocapture which would be performed at spaced apart times during the normal pacing operation of the device while in a bipolar electrode configuration. The autocapture is conducted with primary pulses of a bipolar electrode configuration, back-up pulses from the bipolar electrode configuration, and sensing with the bipolar electrode configuration. As previously explained, during autocapture, the capture threshold is determined. After autocapture is run, the process advances to decision block 120 wherein it is determined if the bipolar capture threshold is above a preset threshold level. If it is not, the process returns to await the running once again of the autocapture. However, if the bipolar electrode configuration capture threshold is too high, the process advances to activity block 124 wherein the impedance measuring circuit 112 is caused to measure the impedance of the bipolar electrode configuration. This impedance measurement is implemented to determine if the cause of the high capture threshold is a possible lead failure of the type, for example, as previously described. Once the impedance is measured in activity block 124, the process advances to decision block 126 wherein the comparator 64 compares the measured impedance to a lower and upper limit to determine if the measures bipolar electrode configuration impedance is within a given impedance range. The impedance range, as previously mentioned, may be between 200 and 2000 ohms. If the lead impedance is outside of the given impedance range and thus considered abnormal, the process then advances to subroutine 128 for responding to the abnormal impedance measurement. The response of subroutine 128 is conducted in a manner which assumes a lead failure in the bipolar electrode configuration and is conducted to assure continued pacing and safety of the patient. Various responses to the abnormal impedance measurement are possible and illustrative subroutines embodying the present invention will be described hereinafter with future reference to FIGS. 4-6. Upon completion of the response to the abnormal impedance measurement, the process returns.

If in decision block 126 it is determined that the impedance is within the given range and therefore normal, it will be noted that the high capture threshold is not due to an impedance failure but is a genuine high threshold for capture. To assure future capture, the process advances to activity block 130 wherein, while still in the bipolar electrode configuration, the output control 66 causes the output of the pulse generator to be increased to a level which assures capture of the heart chamber. The output may be increased, for example, to the maximum pacing output of the device.

Once the output is increased in accordance with activity block 130, the autocapture then periodically runs to measure the capture threshold. As a result, the process advances to decision block 132 wherein it is determined if it is time for a capture threshold assessment by the autocapture 75. If it is, the process advances to decision block 133 wherein the autocapture is run and it is determined if the capture threshold is below a set threshold indicating that the capture threshold has returned to an acceptable level. If the capture threshold has not returned to below the set threshold, the process returns to activity block 124 wherein the impedance measuring circuit 112 is caused to measure the impedance of the bipolar electrode configuration again. Once the impedance is measured in activity block 124, the process advances to decision block 126 wherein the comparator 64 compares the measured impedance to a lower and upper limit to determine if the measured bipolar electrode configuration impedance is within a given impedance range. If the lead impedance is outside of the given impedance range and thus considered abnormal, the process then advances to subroutine 128 for responding to the abnormal impedance measurement as described above. If the lead impedance is within the given impedance range and thus considered normal, the process advances to decision block 132 to await the next capture threshold assessment. However, if the capture threshold has fallen to below the set threshold, the process advances to activity block 134 wherein the pacing output is set in a manner consistent with the measured capture threshold and the selected safety margin as previously described. The process then returns.

Figure 4:
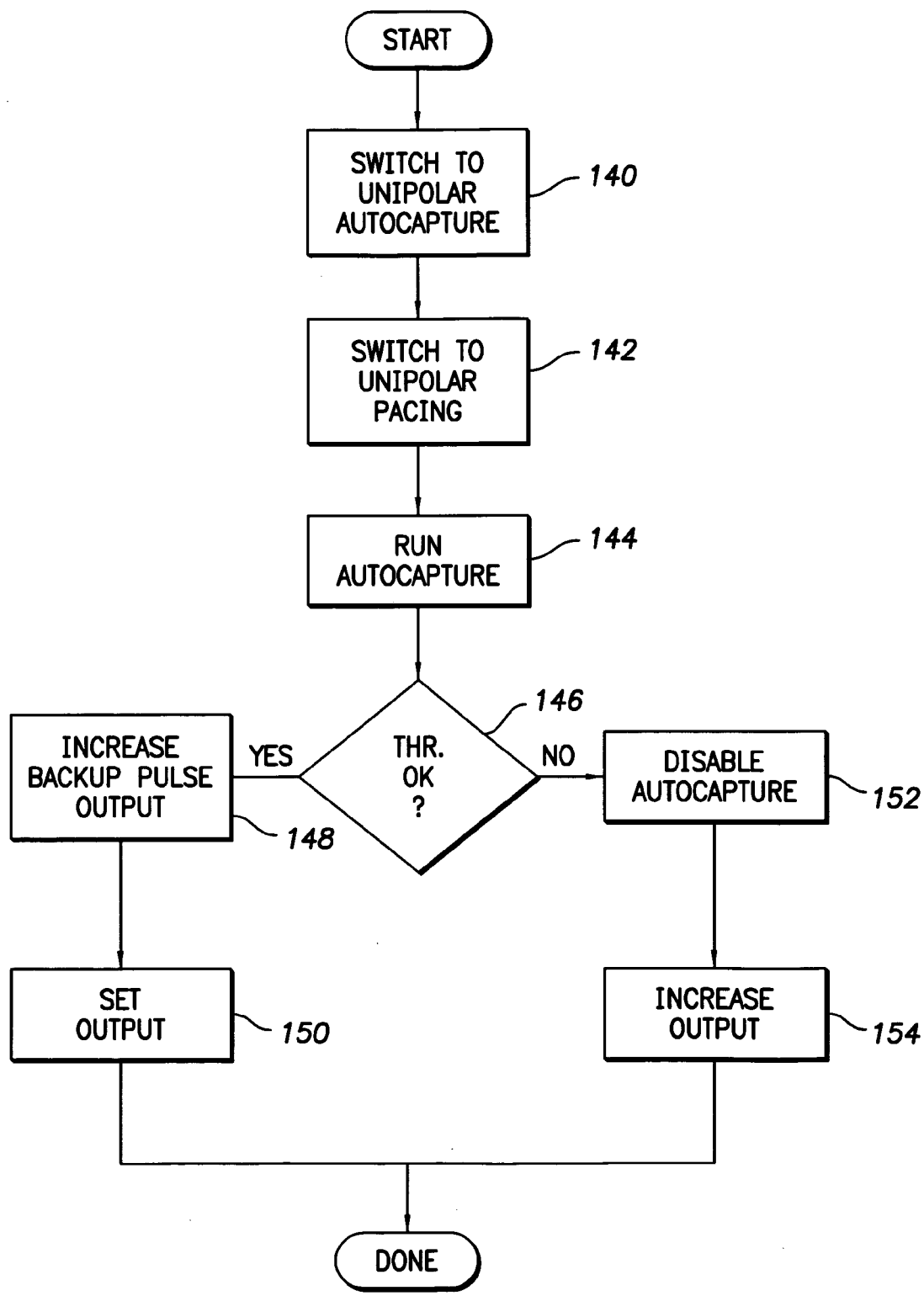
FIG. 4 is a subroutine flow chart describing a first embodiment for responding to an abnormal bipolar electrode configuration impedance measurement.

Referring now to FIG. 4, it illustrates a flow diagram of one subroutine for responding to an abnormal impedance measurement embodying the present invention. After it is determined that the bipolar electrode configuration impedance is abnormal, and hence outside of the given impedance range, the subroutine of FIG. 4 initiates with activity block 140 wherein the electrode configuration control 62 switches the autocapture to unipolar autocapture to provide primary pulses with a unipolar electrode configuration, back-up pulses with a unipolar electrode configuration, and evoked response sensing with a unipolar electrode configuration. The process then advances to activity block 142 wherein the autocapture causes the switch 74 to couple the pulse generator to the unipolar electrode pacing configuration and the sense amplifier to the unipolar electrode configuration to support unipolar pacing. The process then advances to activity block 144 wherein the autocapture 75 assesses the capture threshold of the heart chamber with the unipolar electrode configuration.

After the autocapture of activity block 144, the process advances to decision block 146 wherein it is determined if the capture threshold of the unipolar electrode configuration is below a given threshold indicating a normal capture threshold. If the capture threshold is below the given threshold, the process then advances to activity block 148 wherein the output control increases the output of the unipolar back-up pulse. The output of the unipolar back-up pulse is increased to a point where the patient will perceive the back-up pulse when back-up pulses are applied during future capture threshold assessments. The perceiving of the back-up pulses by the patient will notify the patient that the device is in a unipolar pacing configuration and that there was a possible lead failure which should be reported to the patient's physician. After the back-up pulse output is increased in accordance with activity block 148, the process advances to activity block 150 wherein the unipolar pacing output is adjusted consistent with the measured capture threshold and the selected safety margin. The process then returns.

If in decision block 146 it is determined that the capture threshold is above the given threshold, the process advances to activity block 152 to disable autocapture 75. The output control 66 then in activity block 154 increases the output of the unipolar pacing pulses to a level which assures capture of the heart chamber and which will be perceived by the patient so as to notify the patient of the need for a physician follow-up. The process then returns.

Figure 5:
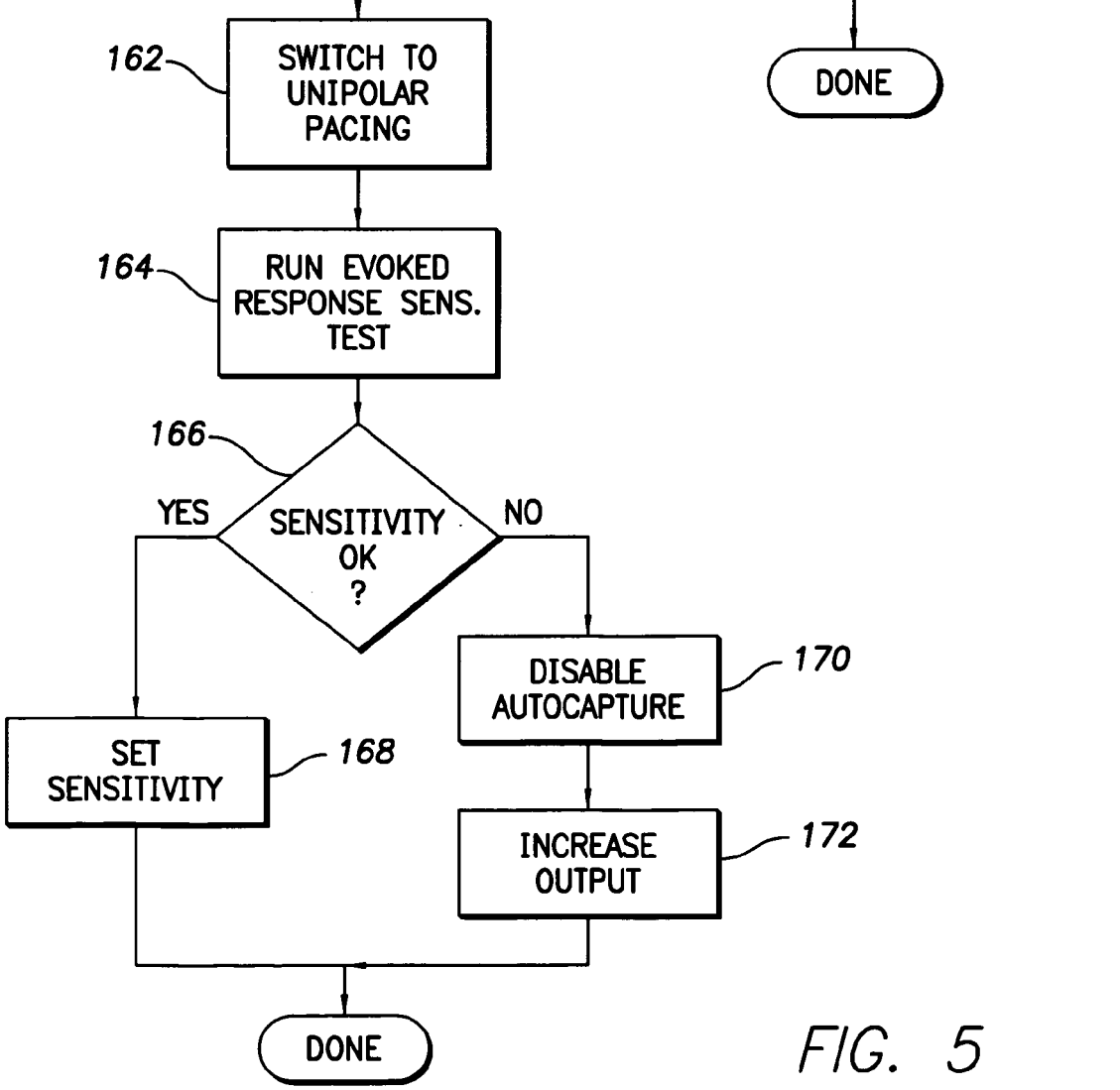
FIG. 5 is a subroutine flow chart describing a second embodiment for responding to an abnormal bipolar electrode configuration impedance measurement.

Referring now to FIG. 5, it illustrates a flow diagram of a second embodiment for responding to an abnormal impedance measurement of the bipolar electrode configuration. The process of the subroutine of FIG. 5 initiates with activity block 160 wherein the autocapture 75 switches the capture threshold assessment to a unipolar electrode configuration. Hence, future autocapture will be with unipolar primary pulses, unipolar back-up pulses, and unipolar evoked response sensing.

The process then advances to activity block 162 wherein the autocapture 75 switches the pulse generator and sense amplifier to the unipolar electrode configuration to provide unipolar pacing. Then, in activity block 164, the autocapture runs an evoked response sensitivity test. In the evoked response sensitivity test, the amplitude of the evoked responses and the amplitude of the polarization is measured. The process then advances to decision block 166 wherein it is determined if the measured evoked response and polarization signals are sufficient to activate autocapture based on the available sensitivities. If they are, the process advances to activity block 168 wherein the autocapture 75 sets the sensitivity of the evoked response detector 77 to an acceptable level. The process then returns to support unipolar pacing and unipolar autocapture.

If in decision block 166 it is determined that the evoked response sensitivity is not appropriate for future autocapture, the process advances to activity block 170 wherein the autocapture 75 is disabled. Then, the process advances to activity block 172 to increase the output of the unipolar pacing pulses to a level to assure capture of the chamber and to a level which may be perceived by the patient as notification of a need for a physician consultation. The process then returns.

Figure 6:
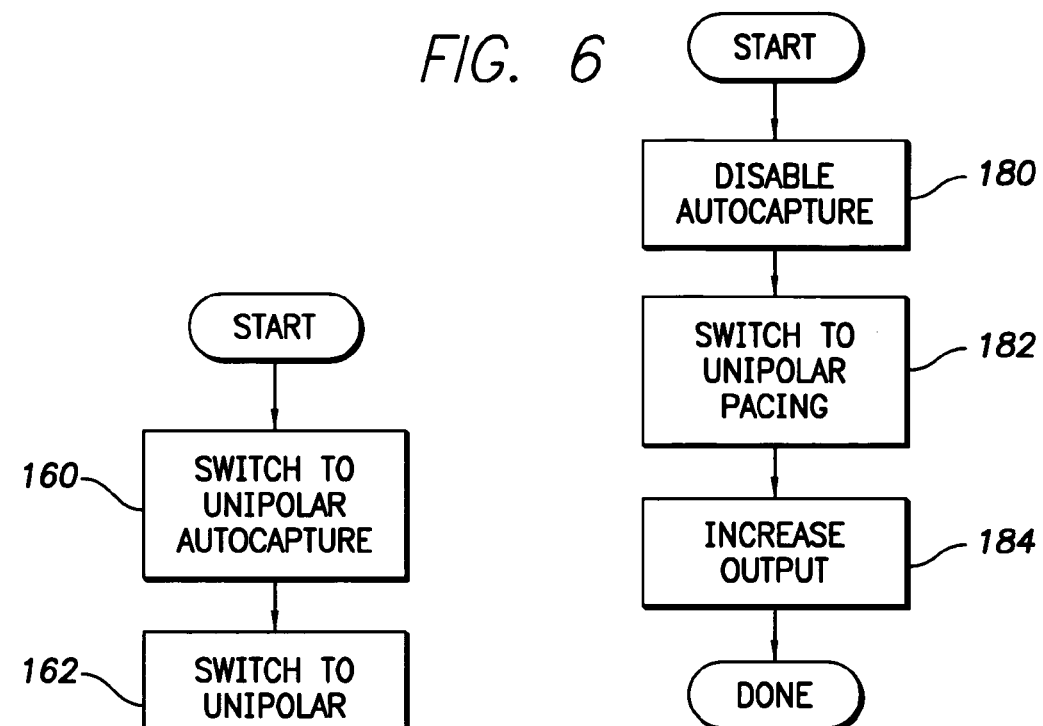
FIG. 6 is a subroutine flow chart describing a third embodiment for responding to an abnormal bipolar electrode configuration impedance measurement.

Referring now to FIG. 6, it illustrates a further embodiment for responding to an abnormal bipolar electrode configuration impedance measurement. The subroutine of FIG. 6 initiates with activity block 180 wherein the autocapture 75 is immediately disabled. The process then advances to activity block 182 wherein the electrode configuration control switches the pulse generator and associated sense amplifier to the unipolar pacing electrode configuration to provide unipolar pacing. The process then advances to activity block 184 wherein the pacing pulse output is increased by the output control 66 to a level which will assure capture of the heart chamber and perception of the pacing pulses by the patient for notification of the need for a physician consultation. The process then completes.

In each of the subroutine embodiments of FIGS. 4-6, the processes there described may be utilized for either ventricular pacing or atrial pacing. As a result, an atrial bipolar electrode configuration may include electrodes 21 and 22 and a unipolar atrial electrode configuration may include electrode 22 and the case 40 of the device 10. For ventricular autocapture, the bipolar electrode configuration may include electrodes 32 and 34 and the unipolar electrode configuration may include electrode 32 and case 40 of the device 10.

As can be seen from the foregoing, the present invention provides bipolar capture threshold assessment while also providing a means by which potential lead failures may be addressed while also assuring continued pacing and safety of the patient. If the bipolar capture threshold is a truly high threshold, without a lead failure, the patient is protected by pacing at a high output level as long as there is a high threshold. When the capture threshold decreases to a normal level, the output of the pacing pulses may be correspondingly decreased to an output commensurate with the measured capture threshold and selected safety margin.

If on the other hand a high bipolar capture threshold is precipitated by a possible lead failure evidenced by a measured bipolar electrode configuration impedance outside of a given and normal range of impedances, the present invention provides responses to this condition which also assures continued pacing of the patient. Further, each of the responses provides a means by which notification is provided to the patient of an abnormal condition requiring a physician consultation. Hence, the present invention renders it possible to provide bipolar autocapture while assuring continued pacing and safety of the patient.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac device that provides autocapture and lead impedance assessment comprising:
   a pulse generator that provides pacing stimulation pulses;
   a sensing circuit that senses cardiac activity;
   a lead system that provides a bipolar electrode configuration and a unipolar electrode configuration associated with a chamber of a heart;
   wherein the pulse generator and sensing circuit are operative to provide pacing therapy with the bipolar electrode configuration;

a capture threshold assessment circuit that measures capture threshold and that couples the pulse generator and sensing circuit to the bipolar electrode configuration to provide bipolar pacing pulses and bipolar evoked response sensing;

an impedance measuring circuit that measures impedance of the bipolar electrode configuration responsive to the assessment circuit measuring a capture threshold above a preset threshold value;

a comparison circuit that determines if the impedance of the bipolar electrode configuration is within a given range; and an electrode configuration control that causes the pacing therapy provided by the pulse generator and the sensing circuit to be switched to the unipolar electrode configuration responsive to the impedance being outside the given range;

wherein the capture threshold assessment circuit couples the pulse generator and sensing circuit to the unipolar electrode configuration to provide unipolar primary pulses, unipolar backup pulses, and unipolar evoked response sensing during pacing therapy.

2. The device of claim 1 further comprising an output control that increases pulse generator output responsive to the impedance being within the given range.

3. The device of claim 2 wherein the output control increases pulse generator output to a maximum level.

4. The device of claim 2 wherein the capture threshold assessment circuit measures the capture threshold responsive to the output control increasing the pulse generator output.

5. The device of claim 4 wherein the output control adjusts the pulse generator output when the measured capture threshold is below a set threshold value.

6. An implantable cardiac device that provides autocapture and lead impedance assessment comprising:

a pulse generator that provides pacing stimulation pulses;

a sensing circuit that senses cardiac activity;

a lead system that provides a bipolar electrode configuration and a unipolar electrode configuration associated with a chamber of a heart;

the pulse generator and sensing circuit providing pacing therapy with the bipolar electrode configuration;

a capture threshold assessment circuit that measures capture threshold and that couples the pulse generator and sensing circuit to the bipolar electrode configuration to provide bipolar primary pulses, bipolar backup pulses and bipolar evoked response sensing during the autocapture test;

an impedance measuring circuit that measures impedance of the bipolar electrode configuration responsive to the assessment circuit measuring a capture threshold above a preset threshold value; and an electrode configuration control that couples the pulse generator and sensing circuit to the unipolar electrode configuration to provide unipolar primary pulses, unipolar backup pulses, and unipolar evoked response sensing during pacing therapy when the impedance is outside a given impedance range.

7. A method of performing an automatic capture test comprising:

providing pacing stimulation therapy to a chamber of a heart with a bipolar electrode configuration;

performing the automatic capture test and determining if capture threshold by the bipolar electrode configuration is above a preset threshold value, the automatic capture test comprising providing bipolar pacing pulses and bipolar evoked response sensing;

measuring bipolar electrode configuration impedance if the capture threshold is above the preset value; and automatically discontinuing pacing stimulation therapy with the bipolar electrode configuration and initiating pacing stimulation therapy with a unipolar electrode configuration to provide unipolar primary pulses, unipolar backup pulses, and unipolar evoked response sensing when the bipolar electrode configuration impedance is above the preset value.

8. The method of claim 7 and further comprising setting stimulation therapy output with the unipolar electrode configuration to a level assuring capture of the chamber of the heart.

9. The method of claim 7 and further comprising determining if the capture threshold by the unipolar electrode configuration is below the preset value.

10. The method of claim 9 and further comprising terminating capture threshold assessment and increasing stimulation output to a level assuring capture in response to a determined capture threshold above the preset value.

11. The method of claim 7 and further comprising increasing pacing stimulation output to a preset output level assuring capture of the chamber when the impedance is within the given impedance range.

12. The method of claim 11 wherein the preset output level is a maximum level.

13. The method of claim 11 and further comprising assessing capture threshold and resetting the stimulation output when the capture threshold is below the preset value.

* * * * *